United States Patent [19]

Schlein

[11] Patent Number: 4,948,585

[45] Date of Patent: Aug. 14, 1990

[54] WASHCLOTH CONTAINING CLEANSING AGENT

[76] Inventor: Allen P. Schlein, 107 Curtis Ter., Fairfield, Conn. 06432

[21] Appl. No.: 358,176

[22] Filed: May 26, 1989

[51] Int. Cl.⁵ .............................................. A61K 9/08
[52] U.S. Cl. .................................... 424/404; 424/401; 424/402; 428/284; 428/286; 428/287; 428/913
[58] Field of Search ........................ 424/401, 402, 404; 428/284, 286, 287, 913

[56] References Cited

U.S. PATENT DOCUMENTS

| | | | |
|---|---|---|---|
| 3,728,213 | 4/1973 | Hinz | 424/404 |
| 4,401,712 | 8/1983 | Morrison | 424/404 |
| 4,882,221 | 11/1989 | Bogart et al. | 424/402 |

Primary Examiner—James J. Bell
Attorney, Agent, or Firm—Spencer E. Olson

[57] ABSTRACT

A disposable washcloth, in one embodiment, is formed by impregnating a sheet of non-woven paper with a cured formulation of water activated polyurethane gel, a sudsing detergent, and an aqueous solution of a medicated cleansing agent, and in another embodiment is made by bonding a sheet of non-woven paper to a sheet of non-woven fabric composed of randomly oriented spray bonded synthetic fibers with the above-mentioned cured formulation. In both cases, the polyurethane dissolves at a slow rate when wetted and controllably releases the detergent and the cleansing agent with modest sudsing.

5 Claims, 1 Drawing Sheet

WASHCLOTH CONTAINING CLEANSING AGENT

BACKGROUND OF THE INVENTION

This invention relates generally to a washcloth for cleansing the body and, more particularly, to a disposable washcloth having a mildly abrasive surface and containing an antiseptic skin cleansing agent suitable for hospital use.

Paper products in sheet form and of a variety of compositions are increasingly being used for cleansing hospital patients in place of more conventional washcloths made of towel-like fabric woven from natural fibers, such as cotton. However, when washing a bed-ridden patient with such paper products, of which the "Handi-Wipe" cloth is an example, the nurse is faced with the problem of how to apply soap or other cleansing agent to the wetted cloth, since one hand usually is being used to prop up the person being washed; needless to say, both hands are needed, one to hold the cloth and the other to rub the wetted cloth with a bar of soap or to pour a quantity of liquid detergent onto the wetted cloth. It would be of great convenience to users of such cloths if the step of applying a cleansing agent to the wetted cloth could be eliminated.

Moreover, washcloths made of paper are extremely soft when wet and lack the abrasion needed for effective removal of soil from the skin, particularly from the skin of a bed-ridden patient who must be bathed with a cloth. As a consequence, nurses often go back to using the somewhat more abrasive toweling material, if available, for both washing and drying the patient's skin. Such cloth towels usually are not disposable, however, instead being laundered after each use, thereby introducing an element of cost which might be avoided by utilizing disposable paper washcloths. Accordingly, there is a need for a disposable washcloth having a mildly abrasive surface, and desirably also containing a cleansing agent, so as to be capable of effectively cleansing soil from a person's skin.

SUMMARY OF THE INVENTION

It is a primary object of the present invention to provide an improved disposable washcloth having a controlled-release cleansing agent incorporated therein.

Another object of the invention is to provide an improved disposable washcloth having a mildly abrasive surface and containing a controlled-release cleansing agent.

Briefly, the washcloth according to one embodiment of the invention has the size and general appearance of a typical paper washcloth and consists of a sheet of non-woven paper impregnated with a cured formulation comprising in selected proportions a water activated polyurethane gel, a sudsing detergent and an aqueous solution of a suitable skin cleansing agent, which formulation dissolves upon contact with washing fluids to release the skin cleanser.

Another embodiment of the washcloth, also having the size and general appearance of a typical paper washcloth, has a first surface consisting of a sheet of suitable non-woven paper and a second surface consisting of a layer of non-woven fabric composed of randomly oriented spray bonded synethetic fibers so as to be mildly abrasive. The sheet of paper and the layer of non-woven fabric are of the same shape and area and are adhesively secured together over substantially their entire surfaces with a cured formulation comprising in selected proportions a water activated polyurethane gel, a sudsing detergent and an aqueous solution of a suitable antiseptic antimicrobial skin cleanser.

In both embodiments the polyurethane essentially traps the molecules of the detergent and the medicated cleansing agent, and prevents it from all being released at once upon immersion of the cloth in a washing fluid, such as water. That is to say, the polyurethane controls the rate of release of the soap whereby a large amount of cleansing agent, more than enough to complete a body bath with one cloth, can be contained in a very thin washcloth of conventional size.

Other objects, features and advantages of the invention, and a better understanding of its construction and method for making it, will be had from the following detailed description, taken in conjunction with the accompanying drawings.

DESCRIPTION OF THE PREFERRED EMBODIMENT

Figure 1:
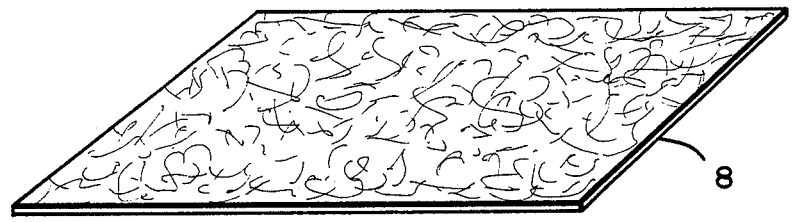
FIG. 1 is a perspective view showing a first embodiment of the washcloth, with its thickness exaggerated for clarity.

Referring to FIG. 1, the washcloth according to the invention in its simplest form consists of a sheet 8 of non-woven material, which may be any of several commercially available papers made of cellulose fibers, of the type typically used for baby bibs, towelettes, towels and impregnated wipers, or made of fine texture rayon or polyester. Examples of the former are the Brand 3030 cellulose papers marketed by Scott Paper Company in its "Hi-Loft" group of "Scott non-wovens", typically having a fabric weight in the range from 1.6 to 2.7 ounces per square yard and a thickness of 27 to 40 mils, and examples of the latter are non-woven papers in Scott's "Dura-tex" line.

A sheet 8 of the selected paper, which is available from vendors in large sheets or rolls, is impregnated with a suitable skin cleansing agent, such as a soap, and then cut up into washcloths of suitable size, six inches by eight being typical. The cleansing agent is added to the washcloth by coating one surface of the sheet of paper with a formulation of water activated polyurethane gel, a sudsing detergent and an aqueous solution of a suitable antimicrobial skin cleanser in such relative proportions as to be highly viscous and mildly foaming when the ingredients are initially mixed together in a foam generator of known construction. Without allowing the polyurethane foam to expand appreciably, the formulation is thinly spread over the entire surface of the paper sheet 8 whereupon it penetrates into the spaces between the non-woven fibers of the paper and then quickly cures and impregnates the paper. An example of a suitable polyurethane gel and examples of suitable cleansing agents for use in the formulation will be discussed below in connection with the description of the embodiment of the washcloth illustrated in FIGS. 2 and 3.

Figure 2:
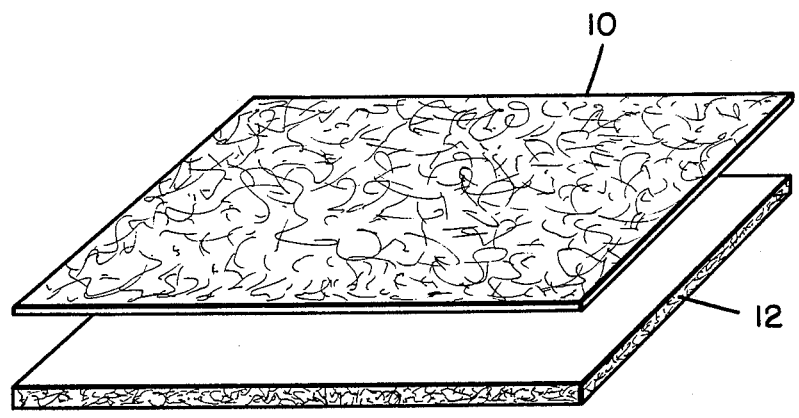
FIG. 2 is a perspective view showing the components, with their thicknesses exaggerated for clarity, of the laminated embodiment of the washcloth prior to lamination.
Figure 3:
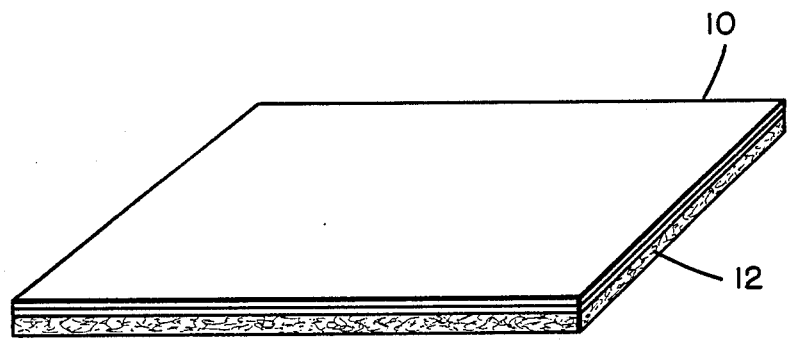
FIG. 3 is a perspective view of the laminated washcloth, ready for use.

Referring to FIG. 2, the washcloth according to another embodiment the invention is formed by bonding a sheet 10 of paper to a sheet 12 of the same shape and size of non-woven synthetic fiber fabric with an adhesive layer 14 consisting of a cured formulation comprising at least a water activated polyurethane gel and an aqueous solution of an antiseptic skin cleanser. The paper sheet 10 may be one of the commercially available papers discussed above, and the layer 12 is preferably a known non-woven, spray-bonded polyester fabric of the type used in such medical applications as surgical gowns, sheets and drapes for operating tables. The material is commercially available from the Loran Products Division of Turco Purex Industrial Corp. of Lawrence, Mass., as its product No. M-93 Light Duty white, and as received from the vendor is approximately 174" thick. Alternatively, non-woven fabrics made with other synthetic fibers such as nylon and dacron may be used.

The sheet 10 of paper is bonded to the fabric sheet 12 with the aforementioned formulation consisting of a water activated polyurethane gel and an aqueous solution of a mildly foaming antiseptic antimicrobial skin cleanser. The polyurethane gel may be HYPOL, a product available from W. R. Grace which has long been used as a vehicle for embedding soap in cellulose sponges. The other constituent may be a mixture of a high sudsing detergent such as Hamposyl, another W. R. Grace product, and any of several commercially available antiseptic antimicrobial skin cleansing preparations of which chlorohexidine gluconate sold by Stewart Pharmaceuticals, a division of I.C.I., under the trademark "Hibitane", and parachlorometaxylenol, sold by Huntington Laboratories, Huntington, Ind., under the trademark "Medi-Scrub", are examples. These agents are preferred over other non-medicated cleansing agents because they leave a film on the skin that is bacteria static for periods up to forty minutes after the skin is washed; accordingly, if a physician's glove should be torn during surgery the patient would still be protected if the surgeon had scrubbed with the present washcloth.

The formulation is prepared by mixing HYPOL polyurethane gel, a very viscous liquid, with the mixture of detergent and selected cleansing agent, in this example, powdered Hamposyl mixed with a 4% solution of "CHG Scrub" marketed by Huntington Laboratories, in the relative proportions:

HYPOL - 50 grams
Powdered Hamposyl - 15 grams
4% solution of "CHG Scrub" 30 grams Immediately upon mixing the ingredients, the mixture starts to foam to produce a foaming liquid which has a viscosity which permits it to be spread as a thin coating. For best results, one surface of a sheet of non-woven polyester fabric is thinly coated with the formulation very soon, on the order of seconds, after mixing, before the polyurethane foam has expanded; the reason for spreading the formulation on the polyester fabric instead of the paper is because of its greater tensile strength and the fact that its more open texture allows better penetration of the formulation into the fabric. The initial tackiness of the formulation holds the two layers together, and then pressure is applied to the laminate to improve the final bond. The thin coating of the formulation, which may be ⅛ inch thick or less, cures in about a minute following application to form a hard, albeit relatively flexible, layer which provides a strong mechanical bond between the paper and fabric layers.

The area of the completed laminate will usually be determined by the size of the rolls or sheet in which the paper selected is available, and is then cut up into individual washcloths of suitable size, six inches by eight inches being typical. One or more of the completed washcloths, shown in FIG. 3, may then be sealed in a suitable package and, if desired, sterilized by ionizing radiation or ethylene oxide gas.

When either embodiment of the washcloth is wetted by a washing fluid, such as water, the cleansing agent is released, with modest sudsing, at a sufficiently slow rate that the contained cleansing agent is more than enough to complete a body bath requiring several immersions of the cloth in the water. The polyurethane in the cured formulation traps molecules of the cleansing agent and, because it dissolves slowly in water, controls the rate of release of the cleansing agent and eliminates the need for applying soap or detergent to the cloth, regardless of the number of times it may be necessary to wet the cloth to do a body bath, and without affecting the bond between the layers in the laminated embodiment. The polyurethane affords a great degree of control of the rate of release of the cleansing agent as compared to the possible, but inferior, alternative of merely spraying soap onto a paper washcloth and drying it, which would provide little or no control.

Although exemplary components of the washcloth have been suggested, and currently preferred constituents of the formulation for adhesively bonding the two components together have been identified, it will now be evident to one skilled in the art that materials other than those specified can be used without departing from the spirit and scope of the invention.

I claim:

1. A disposable washcloth for cleansing a person's skin comprising: a thin flexible sheet of non-woven paper containing a cured formulation comprising in selected proportions a water activated polyurethane gel, a sudsing detergent, and an aqueous solution of an antiseptic antimicrobial skin cleansing agent, said skin cleansing agent being releasable at a controlled rate, with modest sudsing, by dissolution of said polyurethane when the washcloth is wetted by a washing fluid.

2. A washcloth as defined by claim 1, wherein said formulation comprises said polyurethane gel, said detergent, and said solution of skin cleansing agent in such proportions that initially upon being mixed together the formulation foams mildly and has a viscosity which permits it to be thinly spread onto and to penetrate said sheet of paper and that when cured the formulation impregnates the paper.

3. A washcloth as defined by claim 2, wherein said sheet of paper is bonded by said formulation to a flexible layer composed of randomly oriented spray bonded synthetic fibers having a mildly abrasive surface.

4. A disposable washcloth for cleansing a person's skin comprising: a flat laminate consisting of a first layer composed of randomly oriented spray bonded synthetic fibers forming a non-woven fabric having a mildly abrasive surface, and a second layer consisting of a sheet of non-woven paper, said first and second layers being bonded together over substantially their entire area by a cured formulation comprising in selected proportions a water activated polyurethane gel and a mixture of a sudsing detergent and a solution of an antiseptic antimicrobial skin cleansing agent, said detergent and cleansing agent being releasable at a controlled rate, with modest sudsing, by dissolution of said polyurethane when the washcloth is wetted.

5. A washcloth as defined by claim 4, wherein said formulation comprises said polyurethane gel, said detergent, and said solution of skin cleansing agent in such proportions that initially upon being mixed together the formulation foams mildly and has a viscosity which permits it to be thinly spread and to then rapidly cure to form a strong bond between said non-woven fabric and said sheet of paper.

* * * * *